United States Patent
Pan et al.

(10) Patent No.: US 10,520,469 B2
(45) Date of Patent: Dec. 31, 2019

(54) PRINTED FLEXIBLE SENSORS

(71) Applicant: Winbond Electronics Corp., Taichung (TW)

(72) Inventors: Jia-Chyi Pan, Kaohsiung (TW); Zi-Li Kuo, Taichung (TW); Yu-Ting Cheng, New Taipei (TW); Yu-Min Fu, Taoyuan (TW)

(73) Assignee: WINBOND ELECTRONICS CORP., Taichung (TW)

( * ) Notice: Subject to any disclaimer, the term of this patent is extended or adjusted under 35 U.S.C. 154(b) by 0 days.

(21) Appl. No.: 16/400,322

(22) Filed: May 1, 2019

(65) Prior Publication Data

US 2019/0257786 A1   Aug. 22, 2019

Related U.S. Application Data

(62) Division of application No. 15/178,037, filed on Jun. 9, 2016, now Pat. No. 10,345,258.

(51) Int. Cl.

| | |
|---|---|
| *G01N 27/32* | (2006.01) |
| *G01N 27/416* | (2006.01) |
| *G01N 27/30* | (2006.01) |
| *C23C 22/68* | (2006.01) |
| *B05D 7/00* | (2006.01) |
| *B05D 5/12* | (2006.01) |

(52) U.S. Cl.
CPC ....... *G01N 27/4167* (2013.01); *G01N 27/302* (2013.01); *B05D 5/12* (2013.01); *B05D 7/50* (2013.01); *C23C 22/68* (2013.01)

(58) Field of Classification Search
CPC .... G01N 27/302; G01N 27/4167; B05D 5/12; B05D 7/50

USPC .......................................................... 427/58
See application file for complete search history.

(56) References Cited

U.S. PATENT DOCUMENTS

| | | | | |
|---|---|---|---|---|
| 5,702,575 | A * | 12/1997 | Foos | G01N 27/333 204/280 |
| 2002/0029964 | A1 | 3/2002 | Matsumoto | |
| 2009/0320894 | A1 | 12/2009 | Angiuli et al. | |
| 2011/0140703 | A1* | 6/2011 | Chiao | G01N 27/403 324/438 |
| 2011/0278168 | A1* | 11/2011 | Zhuiykov | G01N 27/30 204/407 |

(Continued)

FOREIGN PATENT DOCUMENTS

CN   103517569 A1   1/2014

*Primary Examiner* — Brian K Talbot
(74) *Attorney, Agent, or Firm* — Muncy, Geissler, Olds & Lowe, P.C.

(57) ABSTRACT

A printed flexible PH sensor is provided. The printed flexible PH sensor includes a flexible substrate. A working electrode is disposed on the flexible substrate, and the working electrode includes a first silver layer formed on the flexible substrate by an ink-jet printing process, a second silver layer formed on the first silver layer by a silver mirror reaction, and a metal oxide layer disposed on the second silver layer of an end portion of the working electrode. A reference electrode is disposed on the flexible substrate, and the reference electrode includes the first silver layer and the second silver layer formed on the first silver layer, and a silver chloride layer totally covering the second silver layer. A method for fabricating the printed flexible PH sensor is also provided.

6 Claims, 10 Drawing Sheets

(56) References Cited

U.S. PATENT DOCUMENTS

| | | | |
|---|---|---|---|
| 2013/0245412 A1* | 9/2013 | Rong | A61B 5/14532 600/347 |
| 2014/0027295 A1* | 1/2014 | Chiao | G01N 27/403 205/122 |
| 2016/0202202 A1* | 7/2016 | Wu | G01N 27/302 204/433 |

* cited by examiner

PRINTED FLEXIBLE SENSORS

CROSS REFERENCE TO RELATED APPLICATIONS

This application is a Divisional of co-pending application Ser. No. 15/178,037, filed on Jun. 9, 2016, for which priority is claimed under 35 U.S.C. § 120; the entire contents of all of which are hereby incorporated by reference.

BACKGROUND

Field of the Invention

The present invention relates to PH sensor technology, and in particular to printed flexible PH sensors formed on a flexible substrate and methods for fabricating the same.

Description of the Related Art

PH value is a parameter of the hydrogen-ion concentration in a solution. Glass electrodes are widely used as working electrodes in PH value sensors. Since a glass electrode has such defects as being fragile and corroding easily, at present, the working electrodes of PH value sensors have changed from being glass electrodes to being electrodes made of metals and metal oxides, to overcome the defects of the glass electrodes.

At present, working electrodes and reference electrodes for PH sensors are usually manufactured using electroplating or sputtering, and they provide better conductivity and structure in high-temperature sintering. However, since a flexible substrate cannot withstand high temperatures, manufacturing a working electrode and reference electrode on a flexible substrate to form a flexible PH sensor is not possible using traditional processes.

BRIEF SUMMARY

In some embodiments of the disclosure, a printed flexible PH sensor is provided. The printed flexible PH sensor includes a flexible substrate. A working electrode is disposed on the flexible substrate, and the working electrode includes a first silver layer formed on the flexible substrate by an ink-jet printing process, a second silver layer formed on the first silver layer by a silver mirror reaction, and a metal oxide layer disposed on the second silver layer of an end portion of the working electrode. A reference electrode is disposed on the flexible substrate, and the reference electrode includes the first silver layer and the second silver layer formed on the first silver layer, and a silver chloride layer totally covering the second silver layer.

In some embodiments of the disclosure, a method for fabricating a printed flexible PH sensor is provided. The method includes providing a flexible substrate, forming a first silver layer of a working electrode and a reference electrode on the flexible substrate by a first ink-jet printing process, and performing a silver mirror reaction on the first silver layer to form a second silver layer of the working electrode and the reference electrode. The method also includes forming a metal oxide layer on the second silver layer of an end portion of the working electrode, and forming a silver chloride layer on the second silver layer of the reference electrode.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1A:
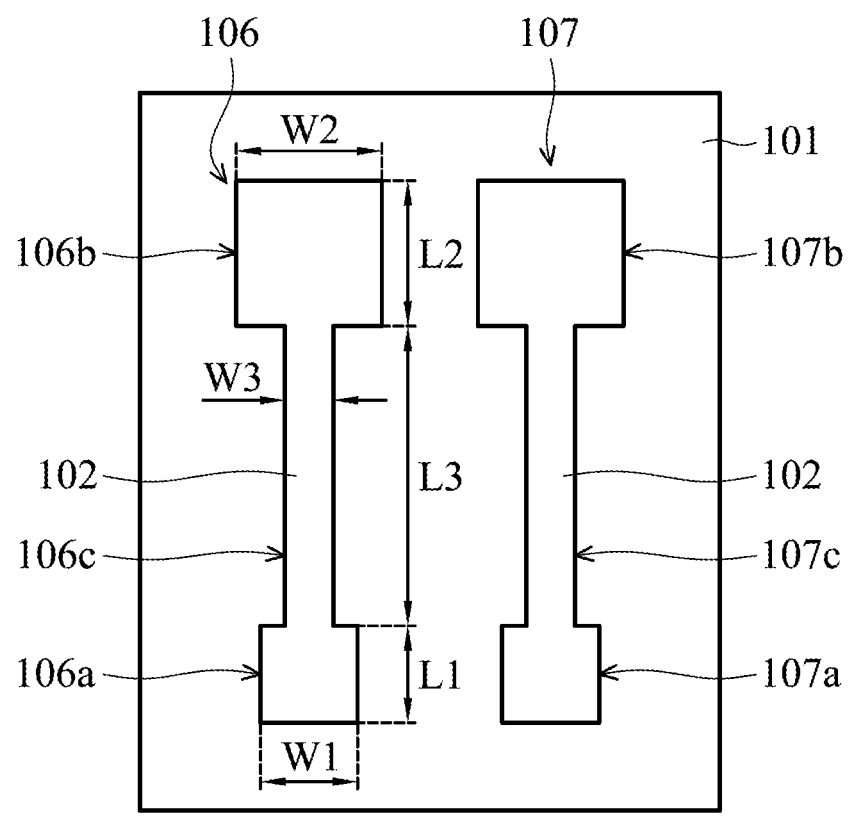
FIGS. 1A-1D show plane views of various stages of a method of fabricating a printed flexible PH sensor according to some embodiments of the disclosure.

The following description is about fabrication and use of a printed flexible PH sensor according to embodiments of the disclosure. However, it should be appreciated that the embodiments of the disclosure provide lots of suitable concepts of the invention and can be performed in a wide variety of specific backgrounds. The specific embodiments of the disclosure are used to explain the fabrication by specific methods and use of the invention and should not be taken in a limiting sense. The scope of the invention is best determined by reference to the appended claims. Moreover, the same or similar elements in the drawings and the description are labeled with the same reference numbers.

Figure 1B:
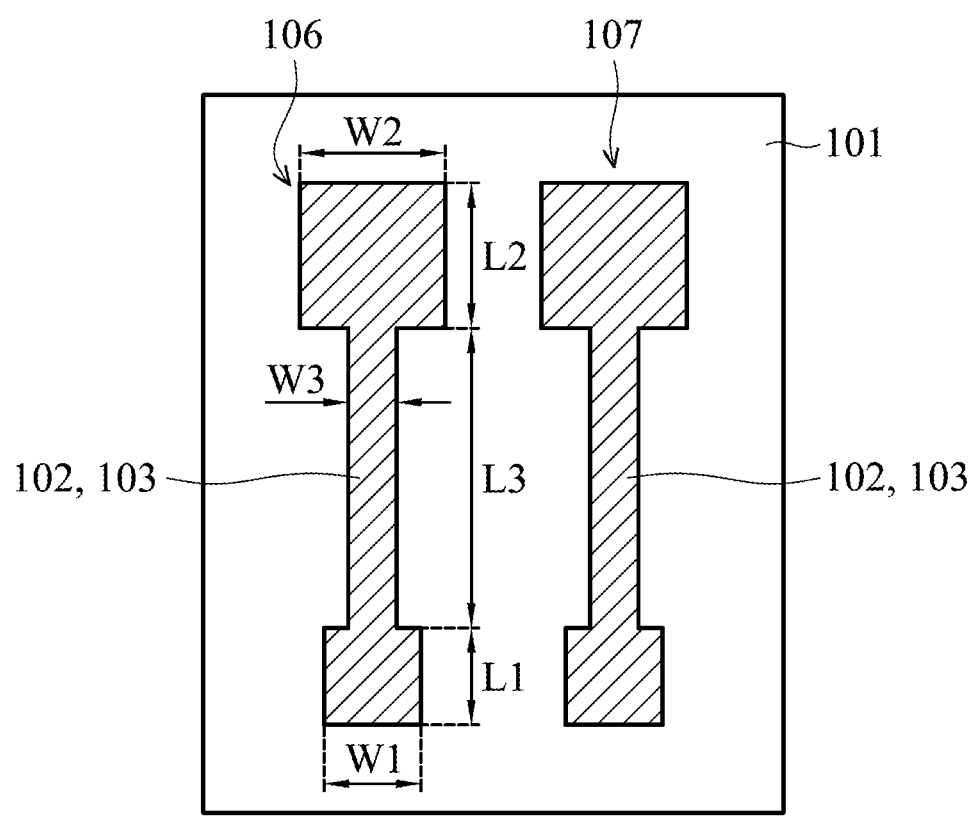
Figure 1C:
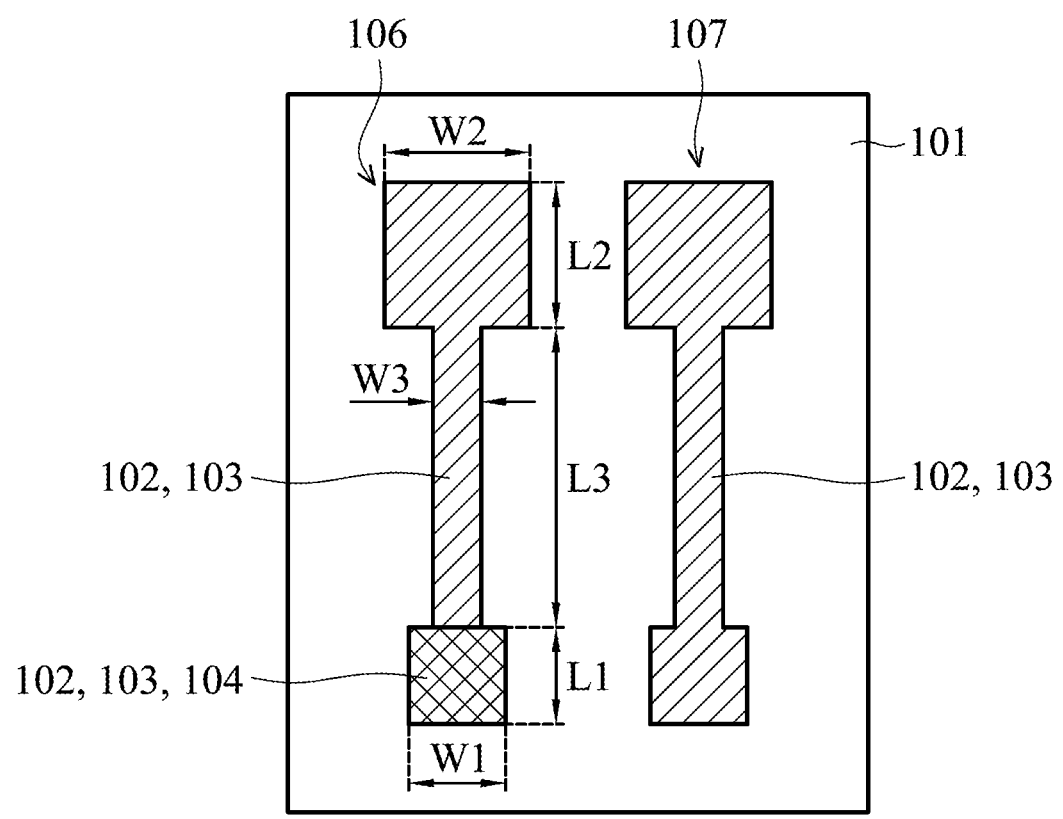
Figure 1D:
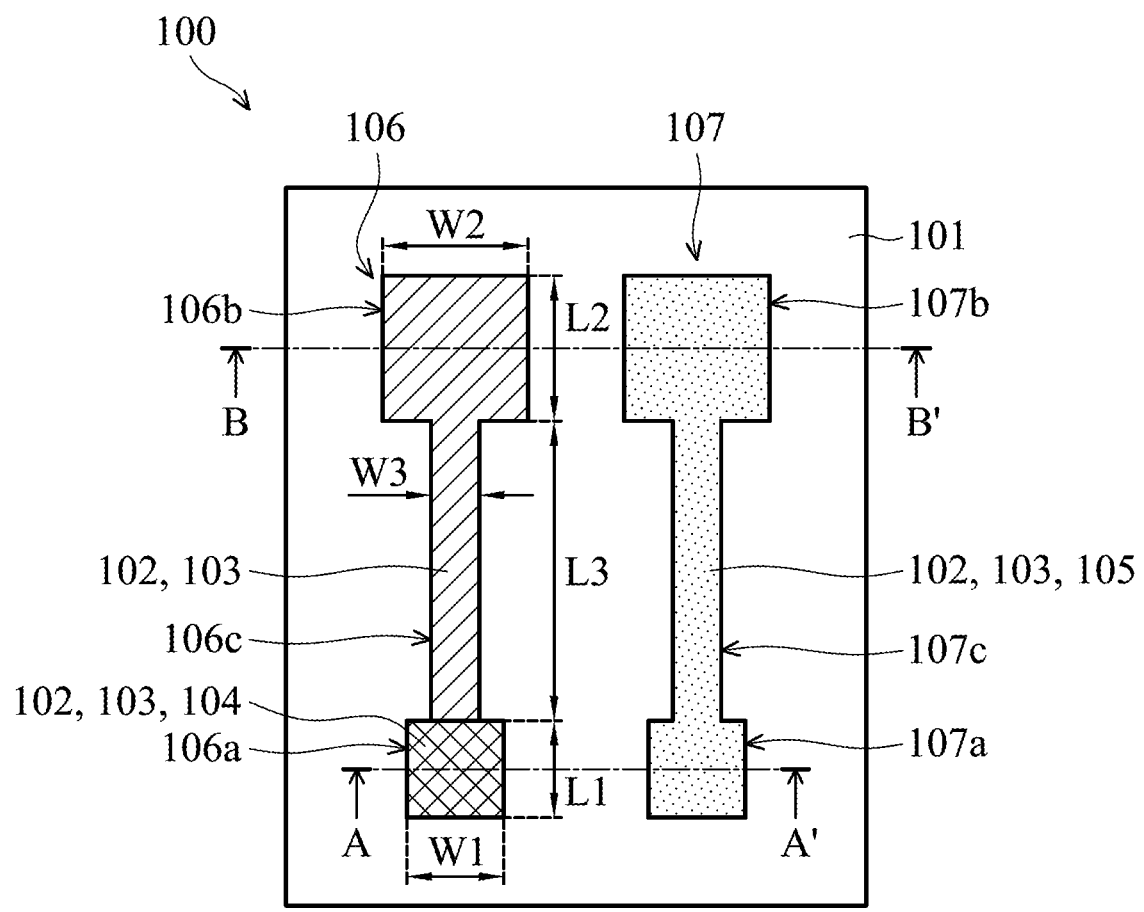

FIGS. 1A-1D show plane views of various stages of a method of fabricating a printed flexible PH sensor 100 (as shown in FIG. 1D) according to some embodiments of the disclosure.

In FIG. 1A, a flexible substrate 101 is provided, and a first silver layer 102 of a working electrode 106 and a reference electrode 107 is formed on the flexible substrate 101. In the embodiment, the method of forming the first silver layer 102 includes an ink-jet printing process. The process temperature of the ink-jet printing process may be below 60° C., but it is not limited thereto. The process temperature of the ink-jet printing process may be determined according to the demands of a particular design. Therefore, the process temperature can be applied to the flexible substrate 101. In some embodiments, the material of the flexible substrate 101 is for example polyethylene terephthalate (PET), polysulfone (PES), polyethylene naphthalate (PEN), polyimide (PI) or polycarbonate (PC) or another suitable flexible material.

The shape of the first silver layer 102 may be determined according to the demands of a particular design by using the ink-jet printing process. Compared to traditional deposition process, photolithography process (including a process of manufacturing a photoresist pattern at front end of the line (FEOL)) and etching process, using the ink-jet printing process to form the first silver layer 102 can eliminate the steps that involve conducting a deposition process, photolithography process and etching process, and can reduce the required materials, thereby reducing manufacturing costs.

In the embodiment, the first silver layer 102 of the working electrode 106 and the reference electrode 107 has the shape of a dumbbell, which has first end portions 106a and 107a, second end portions 106b and 107b, and neck portions 106c and 107c connecting the first end portions and the second end portions. In some embodiments, the size of the first end portions 106a and 107a is smaller than that of the second end portions 106b and 107b. For example, the length L1 and width W1 of the first end portions 106a and 107a are about 1 mm, the length L2 and width W2 of the second end portions 106b and 107b are about 2 mm, the length L3 of the neck portions 106c and 107c is about 3 mm, and the width W3 of the neck portions 106c and 107c is about 0.5 mm, but they are not limited thereto. The lengths and widths of the first end portions 106a and 107a, the second end portions 106b and 107b and the neck portions 106c and 107c of the first silver layer 102 of the working electrode 106 and the reference electrode 107 may be determined according to the demands of a particular design.

In FIG. 1B, a silver mirror reaction is performed on the first silver layer 102 to form a second silver layer 103 of the working electrode 106 and the reference electrode 107. In the embodiment, the second silver layer 103 totally covers the first silver layer 102.

In the silver mirror reaction, since the second silver layer 103 and the first silver layer 102 have the same material, the second silver layer 103 is formed on the first silver layer 102 by small activation energy. Therefore, the silver mirror reaction can be controlled, and performed only on the first silver layer 102 and not on the surface of the flexible substrate 101 by the small activation energy. Compared to a traditional process of deposition, photolithography (including a process of manufacturing a photoresist pattern at the front end of the line (FEOL)) and etching, using the silver mirror reaction to form the second silver layer 103 can eliminate the steps that involve conducting a deposition process, photolithography process and etching process, and can reduce the required materials, thereby lowering manufacturing costs.

Figure 6:
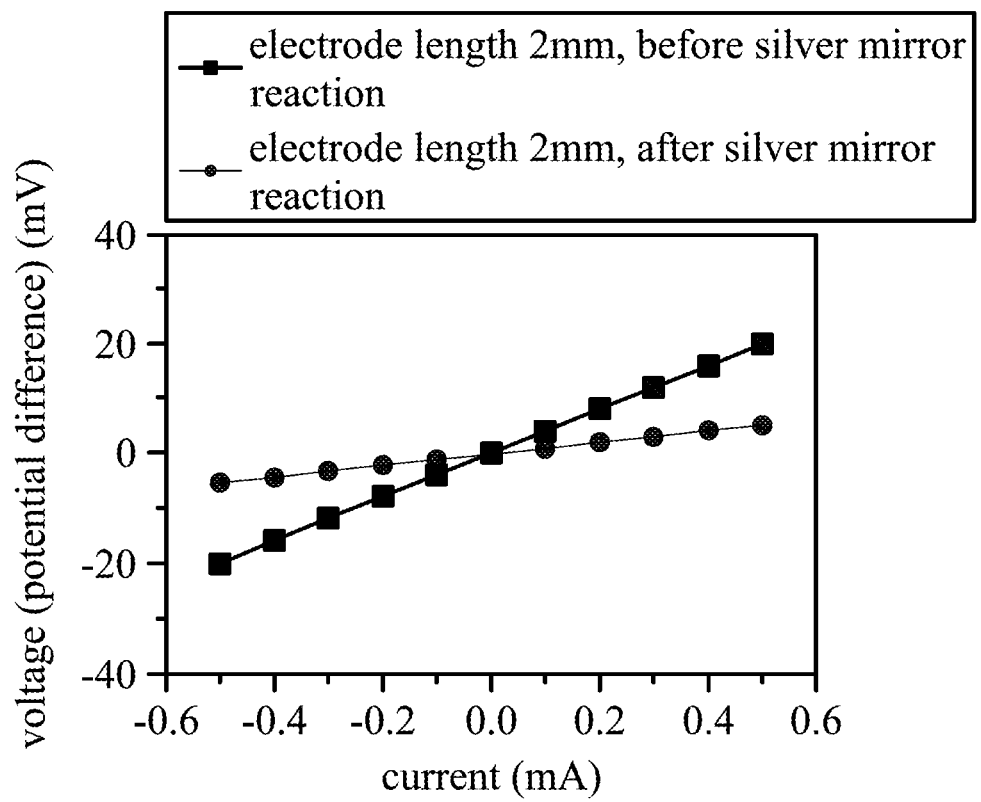
FIG. 6 shows a voltage-current measuring chart of a silver electrode according to some embodiments of the disclosure.

Through the silver mirror reaction, the silver atoms would be in a denser arrangement, and the resistance of silver electrodes formed by the silver mirror reaction is thereby reduced. Therefore, the first silver layer 102 and the second silver layer 103 of the working electrode 106 and the reference electrode 107 have a better conductivity and a better structural strength. Referring to FIG. 6, it shows a voltage-current measuring chart of a silver electrode according to some embodiments of the disclosure. In the embodiment, the length of the silver electrode is 2 mm. As shown in FIG. 6, under the same current, it is known that compared to the silver electrodes prior to performing the silver mirror reaction (for example, the first silver layer 102 of the working electrode 106 and the reference electrode 107), the silver electrodes after the silver mirror reaction (for example, the second silver layer 103 of the working electrode 106 and the reference electrode 107) have a lower voltage (i.e., potential difference). Namely, the silver electrode after the silver mirror reaction has a lower resistance. This proves that the silver mirror reaction improves the conductivity of the first silver layer 102 and the second silver layer 103 of the working electrode 106 and the reference electrode 107.

In some embodiments, the step of performing the silver mirror reaction on the first silver layer 102 includes mixing a silver nitrate ($AgNO_3$) solution and a sodium hydroxide (NaOH) solution to form a first solution, which is the reaction formula (1) of performing the silver mirror reaction. Then, an ammonia ($NH_3$) solution and the first solution are mixed to form a second solution, which is the reaction formula (2) of the silver mirror reaction. Then, the first silver layer 102 of the working electrode 106 and the reference electrode 107 is immersed in the second solution, and a glucose ($C_6H_{12}O_6$) solution is added into the second solution, which is the reaction formula (3) of the silver mirror reaction. As a result, the second silver layer 103 of the working electrode 106 and the reference electrode 107 is formed on the first silver layer 102.

Silver mirror reaction formulas:

$$2Ag^+ + 2OH^- \rightarrow Ag_2O\downarrow + H_2O \qquad (1)$$

$$Ag_2O + 4NH_3 + H_2O \rightarrow 2[Ag(NH_3)_2]^+ + 2OH^- \qquad (2)$$

$$C_6H_{12}O_6 + 2Ag(NH_3)_2OH \rightarrow C_5H_{11}O_5COONH_4 + 2Ag\downarrow + 3NH_3 + H_2O \qquad (3)$$

In the embodiment, the molarity of the silver nitrate solution is between 0.057M and 0.063M, the molarity of the sodium hydroxide solution is between 0.23M and 0.27M, the molarity of the ammonia solution is between 0.19M and 0.21M, the molarity of the glucose solution is between 0.057M and 0.063M, and the volume ratio of the silver nitrate solution, the sodium hydroxide solution, the ammonia solution and the glucose solution is between 6:10:80:2.5 and 6:10:85:3.

In one embodiment, the preparation step of the silver nitrate solution includes dissolving silver nitrate of $1.71*10^{-4}$ mol-$1.89*10^{-4}$ mol in water to 3 ml. The preparation step of the sodium hydroxide solution includes dissolving sodium hydroxide of $1.1875*10^{-3}$ mol-$1.3125*10^{-3}$ mol in water to 5 ml. The preparation step of the ammonia solution includes dissolving ammonia of $7.6*10^{-3}$ mol-$8.4*10^{-3}$ mol in water to 40 ml. The preparation step of the glucose solution includes dissolving glucose of $7.125*10^{-5}$ mol-$7.875*10^{-5}$ mol in water to 1.25 ml.

If the ratio of the glucose solution exceeds the above ratio in the recipe of the silver mirror reaction, lots of silver would be reduced during the silver mirror reaction (the recipe of the silver mirror reaction is the molarity and volume ratio of the silver nitrate solution, the sodium hydroxide solution, the ammonia solution and the glucose solution according to the embodiments of the disclosure). As a result, in addition to the second silver layer 103 being formed on the first silver layer 102, lots of silver would be directly formed on the flexible substrate 101, which is unfavorable for forming the pattern of the working electrode 106 and the reference electrode 107. In addition, if the ratio of the ammonia solution is smaller than the above ratio in the recipe of the silver mirror reaction, ammonia silver complexes would not be formed sufficiently during the silver mirror reaction. As a result, the concentration of the reactants of the silver mirror reaction would be reduced, which is unfavorable for forming the second silver layer 103 of the working electrode 106 and the reference electrode 107. Therefore, using the above recipe ratio of the silver mirror reaction can manufacture the working electrode 106 and the reference electrode 107 effectively.

In FIG. 1C, a metal oxide layer 104 is formed on the second silver layer 103 of the first end portion 106a of the working electrode 106. In the embodiment, an ink-jet printing process can be applied to form the metal oxide layer 104. The process temperature of the ink-jet printing process may be below 60° C., but it is not limited thereto. The process temperature of the ink-jet printing process may be determined according to the demands of a particular design, which is suitable for the flexible substrate 101.

The shape of the metal oxide layer 104 may be determined according to the demands of a particular design by using the ink-jet printing process. Compared to traditional deposition process, photolithography process (including a process of manufacturing a photoresist pattern at front end of the line (FEOL)) and etching process, using the ink-jet printing process to form the metal oxide layer 104 can eliminate the steps that involve conducting a deposition process, photolithography process and etching process, and can reduce the required materials, thereby reducing manufacturing costs.

In FIG. 1D, a silver chloride layer 105 is formed on the second silver layer 103 of the reference electrode 107 and totally covers the two end portions and the neck portion of the reference electrode 107. In some embodiments, the step of forming the silver chloride layer 105 includes immersing the second silver layer 103 of the reference electrode 107 in a first metal chloride solution. In some embodiments, the first metal chloride solution is for example a ferric chloride ($FeCl_3$) solution or a sodium hypochlorite (NaClO) solution, and the molarity of the ferric chloride solution is between $9.5*10^{-2}$ M and $1.05*10^{-1}$ M. The time of the second silver layer 103 of the reference electrode 107 being immersed in the ferric chloride solution is between 15 seconds and 30 seconds.

In some embodiments, after the silver chloride layer 105 of the reference electrode 107 is formed, the silver chloride layer 105 is immersed in a second metal chloride solution to stabilize and saturate the standard potential of the reference electrode 107. In some embodiments, the second metal chloride solution includes a potassium chloride (KCl) solution, and the molarity of the potassium chloride solution is between 2.85M and 3.15M. The time of the silver chloride layer 105 being immersed in the potassium chloride solution is between 171 seconds and 189 seconds.

Through the silver mirror reaction, the first silver layer 102 and the second silver layer 103 can have a better structural density. As a result, in the step of forming the silver chloride layer 105 on the second silver layer 103 of the reference electrode 107, the first silver layer 102 and the second silver layer 103 would not be stripped during the chlorination reaction.

Referring to FIG. 1D, it shows a plane view of the printed flexible PH sensor 100 according to some embodiments of the disclosure. The printed flexible PH sensor 100 includes the working electrode 106 and the reference electrode 107 disposed on the flexible substrate 101. The working electrode 106 and the reference electrode 107 are separated from each other.

Figure 2A:
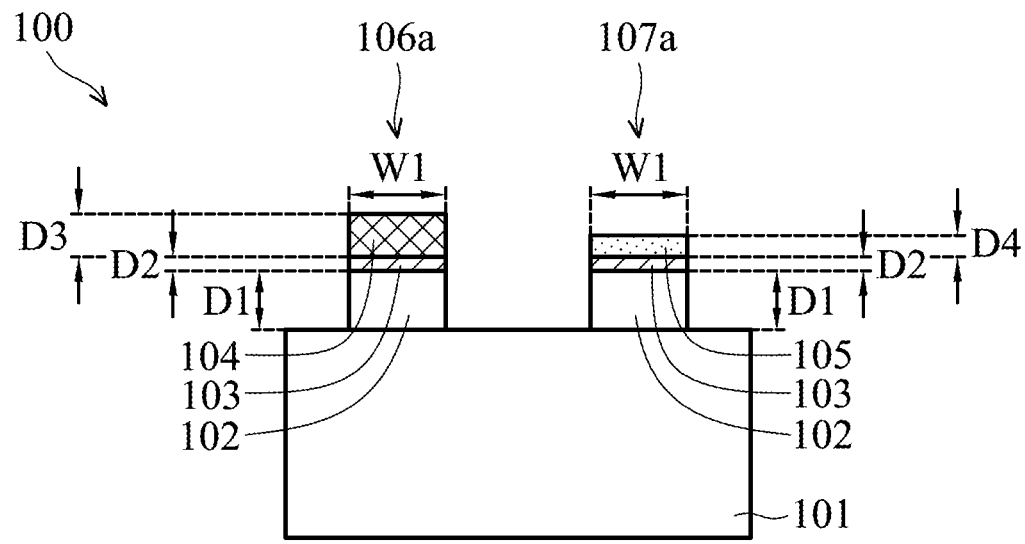
FIG. 2A shows a partial cross section of a printed flexible PH sensor, along the line A-A' shown in FIG. 1D, according to some embodiments of the disclosure.
Figure 2B:
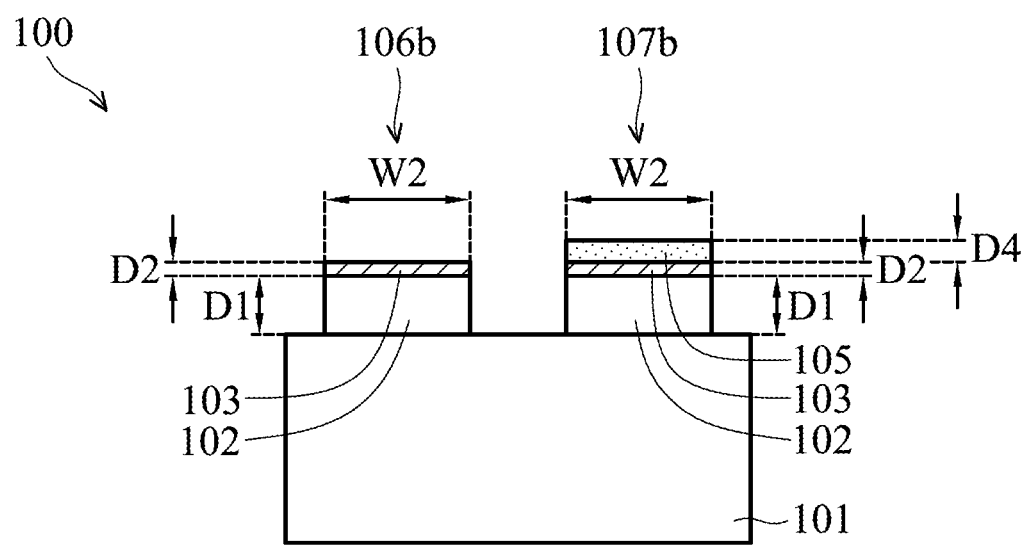
FIG. 2B shows a partial cross section of a printed flexible PH sensor, along the line B-B' shown in FIG. 1D, according to some embodiments of the disclosure.

Referring to FIG. 2A, it shows a cross section of the printed flexible PH sensor 100, along the line A-A' shown in FIG. 1D, according to some embodiments of the disclosure. The line A-A' is along the center line of the first end portions 106a and 107a of the working electrode 106 and the reference electrode 107. The working electrode 106 of the printed flexible PH sensor 100 includes the first silver layer 102 formed on the flexible substrate 101 and the second silver layer 103 formed on the first silver layer 102. In the embodiment, the first silver layer 102 is formed by the ink-jet printing process, and the second silver layer 103 is formed by the silver mirror reaction. In some embodiments, a thickness D1 of the first silver layer 102 is between about 1.2 μm and about 1.5 μm, and a thickness D2 of the second silver layer 103 is between about 5 nm and about 10 nm. In addition, FIG. 2B shows a cross section of the printed flexible PH sensor 100, along the line B-B' shown in FIG. 1D, according to some embodiments of the disclosure. The line B-B' is along the center line of the second end portions 106b and 107b of the working electrode 106 and the reference electrode 107.

Figure 2C:
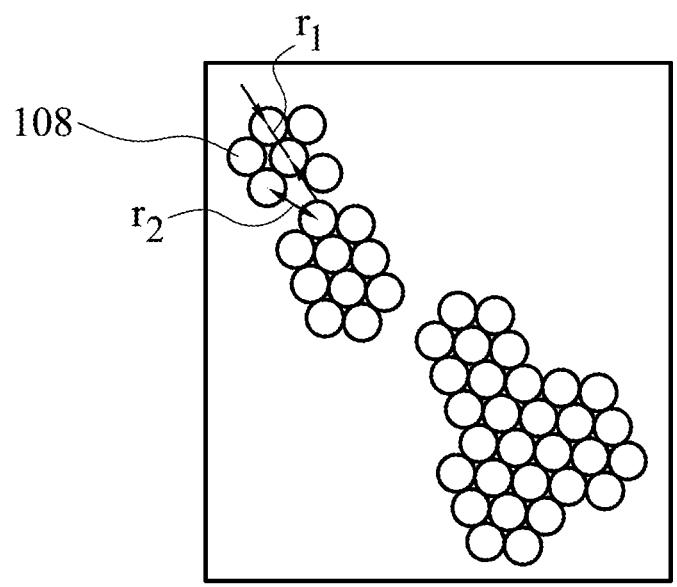
FIG. 2C shows a schematic plane view of silver atoms of a first silver layer and a second silver layer of FIG. 2A observed using a scanning electron microscope (SEM), according to some embodiments of the disclosure.

A schematic plane view of silver atoms of a silver electrode made by traditional high-temperature sintering observed using a scanning electron microscope (SEM) is different from a schematic plane view (as shown in FIG. 2C) of the silver atoms 108 of the second silver layer 103 formed by the silver mirror reaction observed by scanning electron microscopy. Through traditional high-temperature sintering, a plurality of silver atoms would be dissolved together. Namely, two silver atoms at the same level overlap with each other such that the distance between the centers of two silver atoms after being sintered is smaller than a diameter of a silver atom. After a higher temper sintering, the overlapping ratio of two silver atoms at the same level is larger, such that the distance between the centers of two silver atoms after being sintered is even smaller.

According to some embodiments of the disclosure, referring to FIG. 2C, it shows a schematic plane view of silver atoms of the first silver layer 102 and the second silver layer 103 of FIGS. 2A and 2B observed by a scanning electron microscopy, according to some embodiments of the disclosure. Any two adjacent silver atoms 108 at the same level of the second silver layer 103 formed by the mirror silver reaction do not overlap with each other. In some embodiments, a distance r1 between the centers of any two adjacent silver atoms 108 formed by the silver mirror reaction is substantially equal to the diameter of a silver atom 108. In some other embodiments, a distance r2 between the centers of any two adjacent silver atoms 108 formed by the silver mirror reaction may be larger than the diameter of a silver atom 108.

As shown in FIG. 1D, in the embodiment, the metal oxide layer 104 is disposed on the second silver layer 103 of the first end portion 106a of the working electrode 106 and is not disposed on other portions of the second silver layer 103 of the working electrode 106 (as shown in FIG. 2B, above the second silver layer 103 of the second end portion 106b of the working electrode 106 does not have the metal oxide layer 104). In some embodiments, the metal oxide layer 104 includes tungsten trioxide ($WO_3$). In some embodiments, as shown in FIG. 2A, a thickness D3 of the metal oxide layer 104 is between about 0.4 μm and about 0.5 μm. In some embodiments, the metal oxide layer 104 totally covers the two end portions and the neck portion of the second silver layer 103 of the working electrode 106.

As shown in FIG. 2A, the reference electrode 107 of the printed flexible PH sensor 100 includes the first silver layer 102 that is the same as the first silver layer 102 of the working electrode 106. The first silver layer 102 is formed on the flexible substrate 101 by the ink-jet printing process. The reference electrode 107 includes the second silver layer 103 that is the same as the second silver layer 103 of the working electrode 106. The second silver layer 103 is formed on the first silver layer 102 by the silver mirror reaction.

In the embodiment, the silver chloride layer 105 formed on the second silver layer 103 of the reference electrode 107 totally covers the two end portions and the neck portion of the reference electrode 107. In some embodiments, as shown in FIGS. 2A and 2B, a thickness D4 of the silver chloride layer 105 is between about 0.2 µm and about 0.3 µm.

In some embodiments, the first silver layer 102, the second silver layer 103 and the silver chloride 105 of the reference electrode 107 are the same shape and size from a plane view. In addition, the first silver layer 102 and the second silver layer 103 of the working electrode 106 are the same shape and size from the plane view. Furthermore, the metal oxide layer 104 of the working electrode 106 is formed on the first end portion 106a of the working electrode 106.

Figure 3:
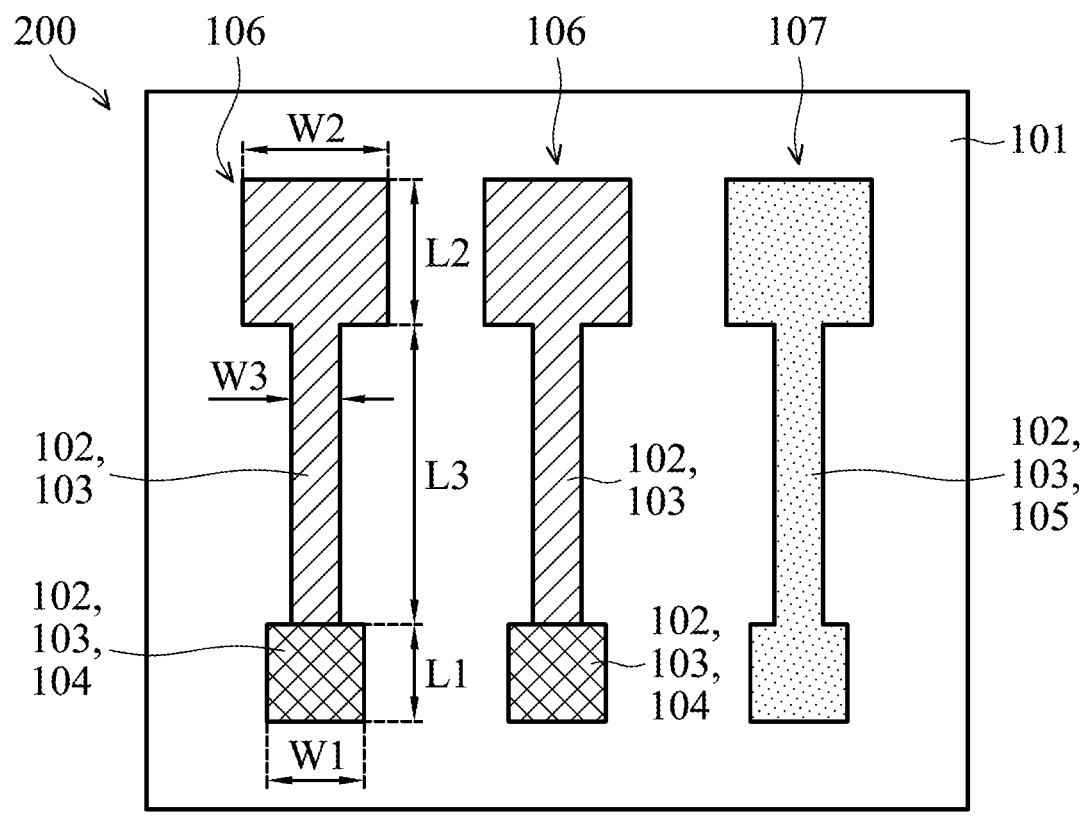
FIG. 3 shows a plane view of a printed flexible PH sensor according to some other embodiments of the disclosure.

Referring to FIG. 3, it shows a plane view of a printed flexible PH sensor 200 according to some other embodiments of the disclosure. Elements of the printed flexible PH sensor 200 in FIG. 3 that are the same as those in FIG. 1D are labeled with the same reference numbers as in FIG. 1D and are not described again for brevity.

The structure of the printed flexible PH sensor 200 shown in FIG. 3 is similar to that of the printed flexible PH sensor 100 shown in FIG. 1D. The difference therebetween is that the printed flexible PH sensor 200 includes multiple working electrodes 106 disposed on the flexible substrate 101. In some embodiments, the printed flexible PH sensor 200 includes multiple working electrodes 106 and one reference electrode 107, but it is not limited thereto. The numbers of the reference electrode 107 may be determined according to the demands of a particular design.

Figure 4:
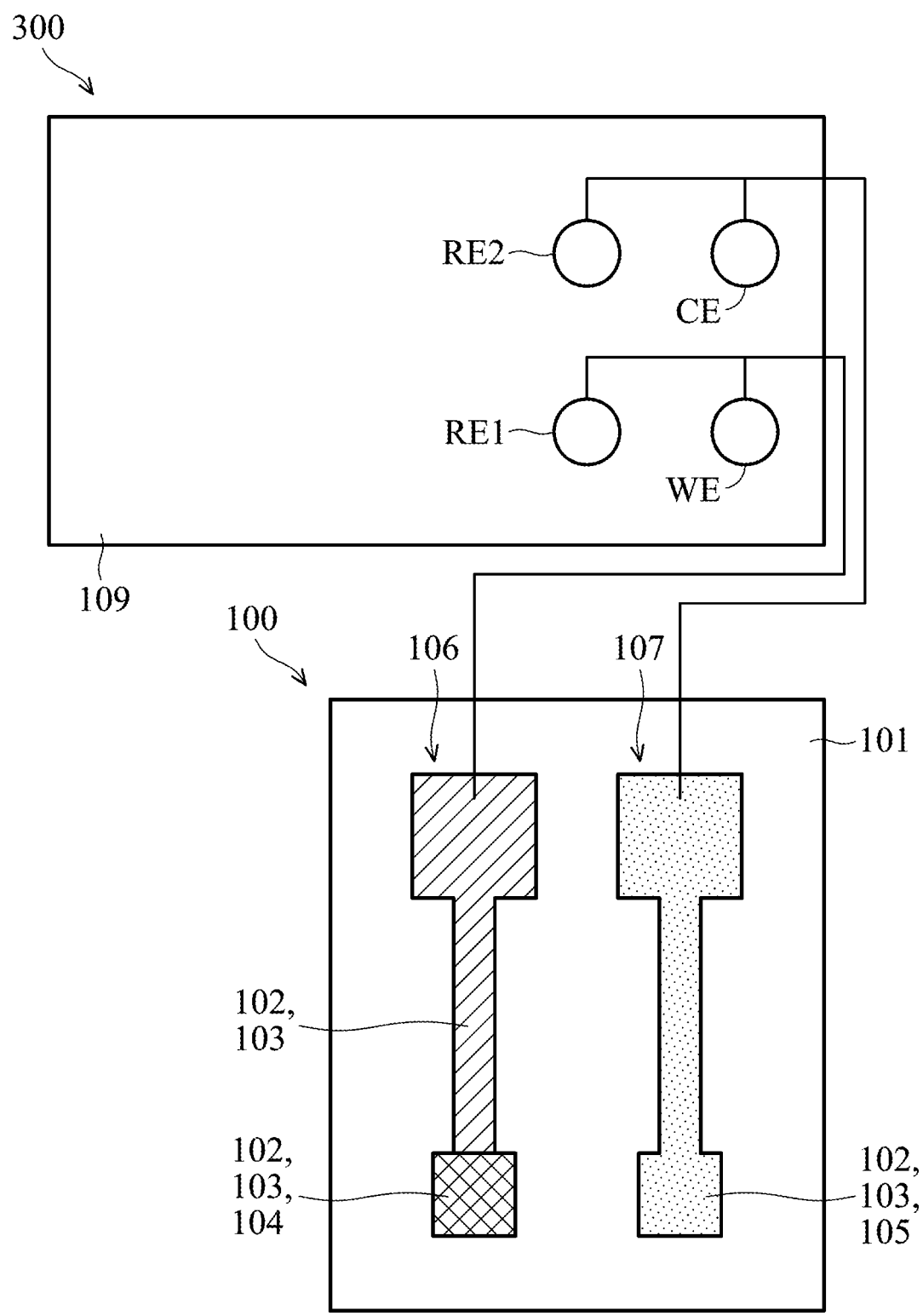
FIG. 4 shows a connection of a PH sensing system according to some embodiments of the disclosure.

Referring to FIG. 4, it shows a connection of a PH sensing system 300 according to some embodiments of the disclosure. Elements of the PH sensing system 300 in FIG. 4 that are the same as those in FIG. 1D are labeled with the same reference numbers as in FIG. 1D and are not described again for brevity.

The structure of the printed flexible PH sensor 100 of the PH sensing system 300 shown in FIG. 4 can be used by taking a structure similar to the printed flexible PH sensor 100 shown in FIG. 1D. In addition, the PH sensing system 300 further includes a potential instrument 109. A working electrode portion WE and a reference electrode portion RE1 of the potential instrument 109 are connected in parallel to the working electrode 106 of the printed flexible PH sensor 100 to measure the potential of the working electrode 106. A compensating electrode portion CE and a reference electrode portion RE2 of the potential instrument 109 are connected in parallel to the reference electrode 107 of the printed flexible PH sensor 100 to measure the potential of the reference electrode 107. Through measuring the potential difference between the working electrode 106 and the reference electrode 107, the potential instrument 109 can covert the potential difference into a PH value.

Figure 5:
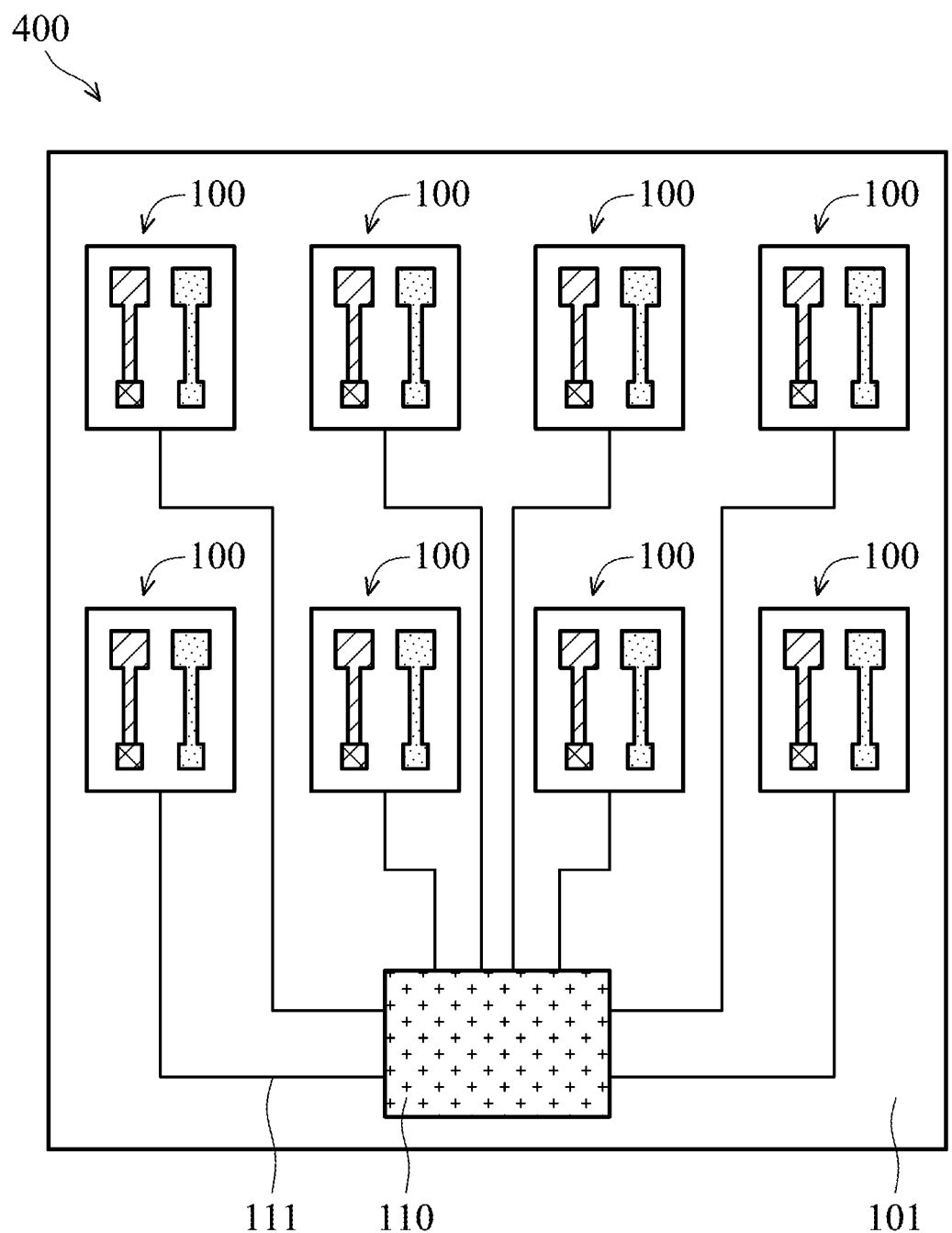
FIG. 5 shows a connection of a PH sensing system according to some other embodiments of the disclosure.

Referring to FIG. 5, it shows a connection of a PH sensing system 400 according to some other embodiments of the disclosure. Elements of the PH sensing system 400 in FIG. 5 that are the same as those in FIG. 1D are labeled with the same reference numbers as in FIG. 1D and are not described again for brevity.

The structure of the printed flexible PH sensor 100 of the PH sensing system 400 shown in FIG. 5 can be used by taking a structure similar to the printed flexible PH sensor 100 shown in FIG. 1D. In addition, the PH sensing system 400 is composed of multiple printed flexible PH sensors 100 and includes a chip 110 disposed on the flexible substrate 101. The chip 110 is connected to the working electrode 106 and the reference electrode 107 of the multiple printed flexible PH sensors 100 by the wires 111, and the chip 110 converts a measured potential difference into a PH value and transfers the PH value to a computer to constitute the concept of an internet of things (IoT). In some embodiments, the chip 110 may include a complementary metal oxide semiconductor (CMOS), a p-type metal oxide semiconductor (PMOS), or a n-type metal oxide semiconductor (NMOS), but it is not limited thereto.

In some embodiments, multiple printed flexible PH sensors 100 can be integrated with the chip 110 by common flip-chip packaging materials such as CuSn or Cu into a wireless sensor tag module.

Figure 7:
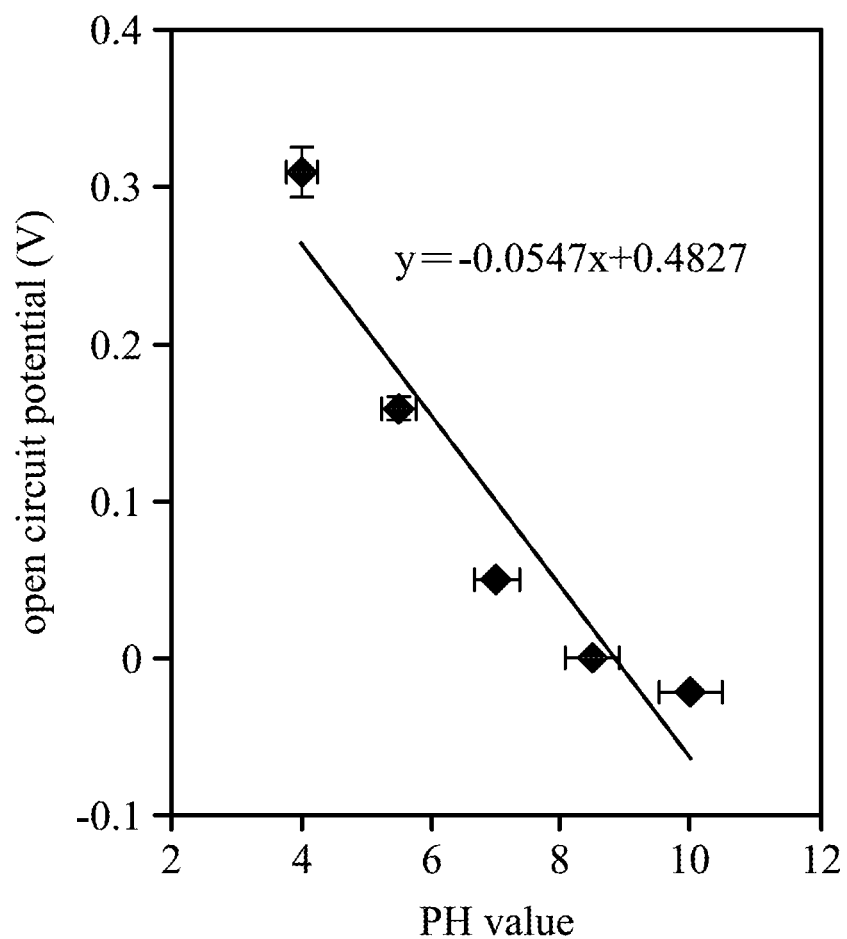
FIG. 7 shows an open circuit potential (OCP)-PH value measuring chart of a printed flexible PH sensor according to some embodiments of the disclosure.

Referring to FIG. 7, it shows an open circuit potential (OCP)-PH value measuring chart of the printed flexible PH sensor 100 according to some other embodiments of the disclosure. The slope of the curve in FIG. 7 indicates the change amount of the open circuit potential is 54.7 mV while the change amount of the PH value measured by the printed flexible PH sensor 100 is 1. It shows that the sensitivity of the printed flexible PH sensor 100 can be 54.7 mV/PH.

According to some embodiments of the disclosure, different from the silver electrode made by traditional high-temperature sintering, the second silver layer formed by the silver mirror reaction has the characteristic of any two adjacent silver atoms at the same level not overlapping with each other.

In addition, using the in-jet printing process to form the first silver layer and the metal oxide layer, the shapes of the first silver layer and the metal oxide layer may be determined according to the demands of a particular design. Moreover, compared to traditional deposition process, photolithography process (including process of manufacturing a photoresist pattern at front end of the line (FEOL)) and etching process, the processes of forming the first silver layer and the metal oxide layer can eliminate the steps that involve conducting a deposition process, photolithography process and etching process, and can reduce the required materials, thereby lowering the cost of manufacturing the PH sensor.

Moreover, since the first silver layer and the second silver layer are made of the same material, in the silver mirror reaction, the second silver layer is formed on the first silver layer through small activation energy. Therefore, the silver mirror reaction can be controlled by the small activation energy to perform only on the first silver layer and not on the surface of the flexible substrate. Compared to traditional deposition process, photolithography process (including a process of manufacturing a photoresist pattern at front end of the line (FEOL)) and etching process, the process of forming the second silver layer can eliminate the steps that involve conducting a deposition process, photolithography process and etching process, and can reduce the required materials, thereby lowering the cost of manufacturing the PH sensor. In addition, through the silver mirror reaction, the silver atoms of the working electrode and the reference electrode would be in a denser arrangement, and the resistance of the silver electrodes is thereby reduced. Therefore, the first silver layer and the second silver layer of the working electrode and the reference electrode have a better conductivity and a denser structure.

In addition, according to some embodiments of the disclosure, the recipe ratio of the silver mirror reaction can prevent lots of silver being reduced and directly formed on the flexible substrate. Therefore, the recipe ratio of the silver mirror reaction of the disclosure can effectively reduce the manufacturing cost of the PH sensor, and it is beneficial to form the pattern of the working electrode and the reference electrode.

Furthermore, compared to the working electrode and the reference electrode of the PH sensor formed by traditional electroplating, sputtering and high-temperature sintering, according to some embodiments of the disclosure, the working electrode is formed by an ink-jet printing process and a silver mirror reaction, and the reference electrode is formed by an ink-jet printing process, a silver mirror reaction and a chlorination reaction. Therefore, the process temperature of forming the PH sensor can be significantly reduced and the working electrode and the reference electrode of the PH sensor can be made on the flexible substrate that cannot resist high temperature, and then the printed flexible PH sensor is formed.

The printed flexible PH sensor and the methods for fabricating the same according to the embodiments of the disclosure can be applied to the food field (for example, frozen food in long-time transportation), the environmental field (for example, PH value detection in rivers), the biomedical field (for example, drug screening, artificial skin monitoring, clinical diagnosis), etc.

While the disclosure has been described by way of example and in terms of the embodiments, it is to be understood that the disclosure is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A printed flexible PH sensor, comprising:
   a flexible substrate;
   a working electrode disposed on the flexible substrate, and the working electrode comprises:
      a first silver layer formed on the flexible substrate by an ink-jet printing process;
      a second silver layer formed on the first silver layer by a silver mirror reaction; and
      a metal oxide layer disposed on the second silver layer of an end portion of the working electrode; and
   a reference electrode disposed on the flexible substrate, and the reference electrode comprises:
      the first silver layer and the second silver layer formed on the first silver layer; and
      a silver chloride layer totally covering the second silver layer.

2. The printed flexible PH sensor of claim 1, wherein any two silver atoms on the same level of the second silver layer do not overlap with each other.

3. The printed flexible PH sensor of claim 1, wherein the working electrode and the reference electrode respectively have a pattern constituted by two end portions and a neck portion connection the two end portions.

4. The printed flexible PH sensor of claim 3, wherein the two end portions of the working electrode are different sizes and the two ends portions of the reference electrode are different sizes, and the metal oxide layer of the working electrode is disposed on the end portion with a smaller size.

5. The printed flexible PH sensor of claim 1, wherein the material of the flexible substrate includes polyethylene terephthalate, polysulfone, polyethylene naphthalate, polyimide or polycarbonate.

6. The printed flexible PH sensor of claim 1, wherein the metal oxide layer includes tungsten trioxide ($WO_3$).

* * * * *